(12) United States Patent
Pursley

(10) Patent No.: US 8,007,489 B2
(45) Date of Patent: Aug. 30, 2011

(54) METHOD AND APPARATUS FOR CURVING A CATHETER

(75) Inventor: Matt D. Pursley, Alpharetta, GA (US)

(73) Assignee: Volcano Corporation, Rancho Cordova, CA (US)

( * ) Notice: Subject to any disclaimer, the term of this patent is extended or adjusted under 35 U.S.C. 154(b) by 1516 days.

(21) Appl. No.: 10/877,424

(22) Filed: Jun. 25, 2004

(65) Prior Publication Data

US 2005/0004555 A1    Jan. 6, 2005

Related U.S. Application Data

(60) Provisional application No. 60/483,867, filed on Jun. 25, 2003.

(51) Int. Cl.
*A61M 25/00* (2006.01)
*A61B 6/01* (2006.01)

(52) U.S. Cl. .......................... 604/528; 600/434

(58) Field of Classification Search ............... 604/96.01, 604/164.01, 523, 500, 528; 600/585, 424
See application file for complete search history.

(56) References Cited

U.S. PATENT DOCUMENTS

| | | | |
|---|---|---|---|
| 2,688,329 A | 9/1954 | Wallace | |
| 3,867,945 A | 2/1975 | Long | |
| 4,033,331 A | 7/1977 | Guss et al. | |
| 4,813,925 A | 3/1989 | Anderson, Jr. et al. | |
| 4,934,340 A | 6/1990 | Ebling et al. | |
| 5,078,684 A | 1/1992 | Yasuda | |
| 5,334,168 A | 8/1994 | Hemmer | |
| 5,603,694 A | 2/1997 | Brown et al. | |
| 5,733,248 A | 3/1998 | Adams et al. | |
| 5,951,539 A * | 9/1999 | Nita et al. ................ | 604/526 |
| 6,030,371 A | 2/2000 | Pursley | |
| 6,053,900 A | 4/2000 | Brown et al. | |
| 6,402,736 B1 | 6/2002 | Brown et al. | |
| 6,447,488 B2 * | 9/2002 | Estabrook et al. ........... | 604/264 |
| 7,037,290 B2 * | 5/2006 | Gardeski et al. .......... | 604/95.01 |
| 7,381,205 B2 * | 6/2008 | Thommen ................ | 604/528 |
| 2002/0156452 A1* | 10/2002 | Pursley et al. ............ | 604/500 |
| 2006/0224142 A1* | 10/2006 | Wilson et al. ............ | 604/510 |

FOREIGN PATENT DOCUMENTS

WO        WO 9632980         * 10/1996

* cited by examiner

*Primary Examiner* — Theodore J Stigell
*Assistant Examiner* — Imani Hayman
(74) *Attorney, Agent, or Firm* — Jeffrey L. Thompson; Thompson & Thompson, P.A.

(57) ABSTRACT

An apparatus and method for curving a catheter after deployment include a catheter having a primary lumen, a secondary lumen, and a resilient fiber contained within the secondary lumen. The resilient fiber and the secondary lumen have corresponding, preformed curve shapes when the catheter is in a straight, unstressed condition. The resilient fiber is slidable within the secondary lumen to create a desired curve shape in the catheter as the curved portion of the resilient fiber slides into an originally straight portion of the secondary lumen. In another embodiment, the preformed curve shape of the resilient fiber is held in a straight condition within a stiff, marker ring segment of the catheter until after the catheter is deployed. Once deployed, the resilient fiber is slid out of the marker ring segment, and the preformed curve shape of the resilient fiber creates a corresponding curve shape in the catheter.

6 Claims, 3 Drawing Sheets

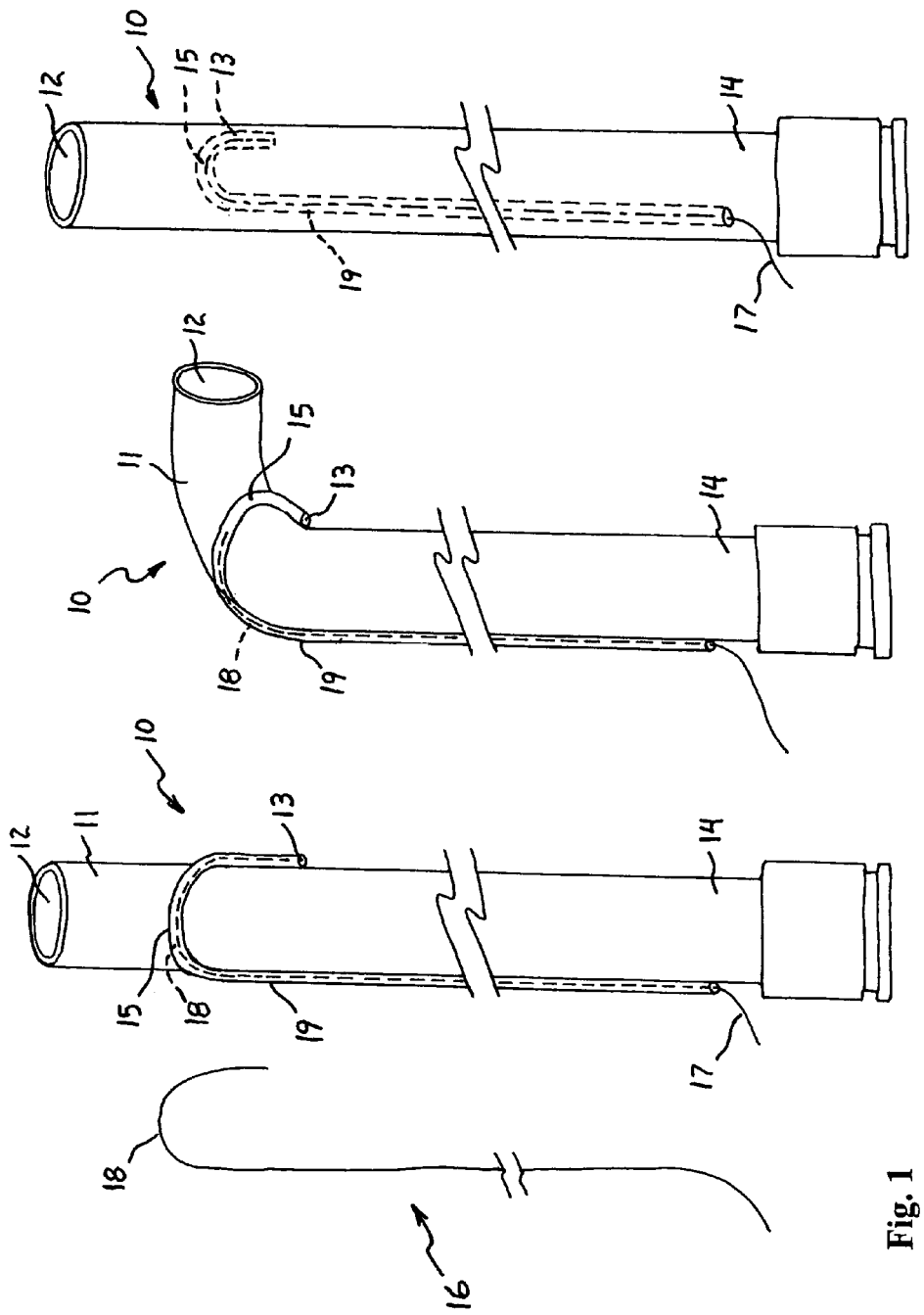

METHOD AND APPARATUS FOR CURVING A CATHETER

RELATED APPLICATIONS

This application claims the benefit of the Applicant's provisional patent Application No. 60/483,867 filed on Jun. 25, 2003, and also relates to the subject matter of Applicant's copending U.S. application Ser. No. 10/167,718 filed on Jun. 11, 2002, which is hereby incorporated by reference.

BACKGROUND OF THE INVENTION

1. Field of the Invention

The present invention relates generally to catheters and, in particular, to catheters that can be curved or bent at their distal ends or other selected locations, and methods for making and deploying such catheters.

2. Description of the Related Art

Catheters frequently have "preset" curves in them to enhance the physician's ability to introduce the catheter to the desired location. Usually, this curve is "set" in the catheter by first bending the catheter to the desired shape, then applying heat to the catheter while in this curved state, and then allowing the catheter to cool while still in this curved shape. The plastic memory of the polymer allows the curved shape to be maintained after cooling. In some cases, the catheter can be curved without heat by cold working the catheter into a curved shape.

The existing methods of curving catheters suffer from a number of disadvantages. First, the curved shape requires some rigidity of the catheter to maintain the curvature. Second, the curve can only be "set" outside of the body. Third, the soft wall of the catheter needed to make the curve shape often becomes crushed or kinked during use. Fourth, a small size and tight curvature of the catheter is difficult to achieve.

Thus, there is a need in the industry for an improved method and apparatus for making and deploying catheters that allow the catheter to be curved or bent at its distal end or other selected locations during deployment.

SUMMARY OF THE INVENTION

It is an object of the present invention to provide a method and apparatus for curving a distal end of a catheter that overcomes the problems in the above-mentioned prior art.

It is a further object of the present invention to provide an improved method for introducing curves into catheters while the catheters remain inside the body.

It is a further object of the present invention to provide a small neuro vascular catheter having a deflectable tip that allows improved positioning within the vascular system for transmitting subsequent diagnostic and therapeutic devices or media.

It is a further object of the present invention to provide an improved method for introducing a curve in a catheter that uses a marker band section at the distal tip of the catheter in conjunction with a precurved distal segment of a resilient filament to create the desired curve in the catheter.

To achieve the foregoing and other objects and in accordance with the purpose of the present invention, as embodied and broadly described herein, a first embodiment of the present invention provides an apparatus and method for curving a catheter having a primary lumen, a secondary lumen, and a resilient fiber contained within the secondary lumen. A portion of the secondary lumen near the distal end of the catheter is nonparallel to the primary lumen and may form, for example, a partial loop configuration relative to the primary lumen. The resilient fiber and the secondary lumen have corresponding, preformed curve shapes when the catheter is in a straight, unstressed condition. The resilient fiber is slidable within the secondary lumen to create a desired curve shape in the catheter as the curved portion of the resilient fiber slides into an originally straight portion of the secondary lumen.

In another embodiment, the resilient fiber is disposed within a channel, and the preformed curve shape of the resilient fiber is held in a straight condition within a stiff, marker ring segment of the catheter until after the catheter is deployed within a patient's body. Once deployed, the resilient fiber is slid out of the stiff, marker ring segment, and the resilient fiber regains its preformed curve shape and creates a corresponding curve shape in a soft, flexible portion of the catheter adjacent to the marker ring segment. A second channel and a second resilient fiber can be used to temporarily straighten the catheter to adjust its position within the patient's body.

Additional objects, advantages, and novel features of the invention will be set forth in the following description, and will become apparent to those skilled in the art upon reading this description or practicing the invention. The objects and advantages of the invention may be realized and attained by the appended claims.

BRIEF DESCRIPTION OF THE DRAWINGS

The present invention will become more clearly appreciated as the disclosure of the present invention is made with reference to the accompanying drawings. In the drawings:

FIG. 1 is a side view of resilient fiber core having a preset curvature near a distal end for use in the present invention.

FIG. 2 is a side view of a catheter according to a first embodiment of the present invention, which includes a primary lumen, an additional lumen attached to the primary lumen, and the resilient fiber core of FIG. 1 contained within the additional lumen in an unstressed state.

FIG. 3 is a side view of the catheter shown in FIG. 2 with the catheter tip being deflected by sliding the resilient fiber core within the additional lumen.

FIG. 4 is a side view of a catheter according to a variation of the first embodiment of the present invention in which the additional lumen is contained within the wall of the primary lumen.

DETAILED DESCRIPTION OF THE INVENTION

Figure 5:
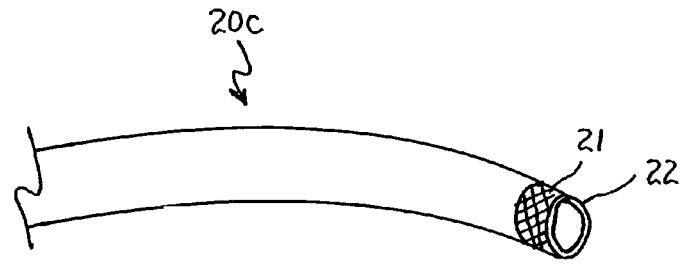
FIG. 5 is a perspective view of a catheter having a marker band located at the distal end of the catheter for visualization during deployment.
Figure 6:
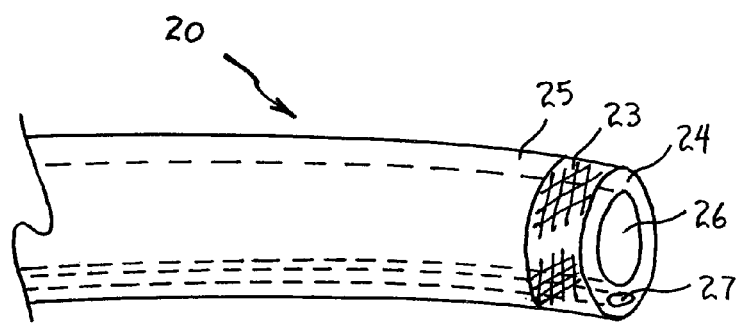
FIG. 6 is a perspective view of a catheter according to a second embodiment of the present invention in which a marker band is located at the distal end of the catheter, and a channel is provided in the wall of the catheter for receiving a resilient fiber core.

Methods and apparatus for curving a distal end of a catheter according to the present invention will be described in detail hereinafter with reference to FIGS. 1 to 10 of the accompanying drawings.

A catheter 10 having a deflectable distal tip 11 according to a first embodiment of the present invention will be described with reference to FIGS. 1 to 4 of the drawings. The catheter 10 includes a primary lumen 12 as in conventional catheters, and a secondary lumen 13 that is either attached to the primary lumen 12 (as shown in FIGS. 2 and 3) or contained within the wall of the primary lumen 12 (as shown in FIG. 4). The secondary lumen 13 transverses the primary lumen 12 from the proximal end 14 of the catheter 10 to near the distal end 11 where it forms a partial loop configuration 15 (e.g., 180 degrees as shown in FIG. 2) and begins to track back toward the proximal end 14 of the catheter 10. Other shapes for the curved portion 15 of the secondary lumen 13 can also be used as long as the secondary lumen 13 has at least a portion near its distal end that is nonparallel to the primary lumen 12; i.e., the distal end of the secondary lumen 13 is curved, bent, or otherwise divergent from a path parallel to the primary lumen 12.

A small diameter, resilient fiber 16 is inserted within the secondary lumen 13. For example, the resilient fiber 16 can be formed of a metallic steel heat-tempered spring alloy, such as a titanium-nickel-chromium alloy, or a boron fiber having a diameter of 0.001 to 0.006 inches. The resilient fiber 16 has an unstressed shape that corresponds to the unstressed shape of the secondary lumen 13, as shown in FIG. 1. The catheter 10 shown in FIG. 2 has the resilient fiber 16 inserted within the secondary lumen 13 and an overall shape which is substantially straight when the resilient fiber 16 and the secondary lumen 13 are in their unstressed states.

The catheter 10 of the present invention is preferably formed of a nylon, urethane, PE, TFE, or other suitable polymer material which is very soft and offers little resistance to the preformed shape of the resilient fiber 16. The catheter 10 can be formed, for example, using the nonextrusion manufacturing method and apparatus described in Applicant's U.S. Pat. No. 6,030,371. Using this method, the catheter 10 can be formed with a variable hardness over its length by continuously changing the constituents or mixtures of the polymer material(s) being used. The catheter can thus have a relatively stiff or hard portion near its proximal end 14 and a relatively softer portion near its distal end 11.

When deflection at the distal tip 11 of the catheter 10 is desired, the resilient fiber 16 is pulled at its proximal end 17 and the curved part 18 of the resilient fiber 16 slides into the straight portion 19 of the secondary lumen 13. As the resilient fiber 16 slides within the straight portion 19 of the secondary lumen 13, that portion of the secondary lumen 13 will begin to take the shape of the curved part 18 of the resilient fiber 16, resulting in a deflected catheter tip 11 as shown in FIG. 3.

The secondary lumen 13 and the resilient fiber 16 are not limited to a 180-degree bend or a single bend, as shown in FIGS. 1 and 2. Instead, multiple bends or bends of different angles in the secondary lumen 13 and the resilient fiber 16 can be used to deflect the catheter 10 in a specific way for a given application or procedure.

The deflectable tip 11 of the catheter 10 according to the first embodiment allows the catheter 10 to remain straight while traversing the vascular system to the desired location within the anatomy. The catheter 10 can then be deflected at a specific angle near the distal tip 11, so that the catheter 10 can be better positioned for transmitting subsequent diagnostic and therapeutic devices or media.

A catheter 20 according to a second embodiment of the present invention will now be described with reference to FIGS. 5 to 10 of the drawings. A conventional catheter 20c having a marker band 21 at its distal end 22 is shown in FIG. 5. The marker band 21 is typically provided for visualization to facilitate positioning the distal end 22 of the catheter 20c within the anatomy.

The catheter 20 according to the second embodiment is shown in FIGS. 6 to 9. The catheter 20 has a marker band 23 at its distal end 24, which can be used for visualization similar to the marker band 21 in the conventional catheter 20c of FIG. 5. The marker band 23 is formed of a hard polymer, while the other part 25 near the distal end of the catheter 20 is formed of a soft, flexible polymer material. The marker band 23 does not affect the overall flexibility of the catheter 20 because it only affects the catheter shaft for a very short region (i.e., the catheter 20 is stiff only where the marker band 23 is located).

Figure 7:
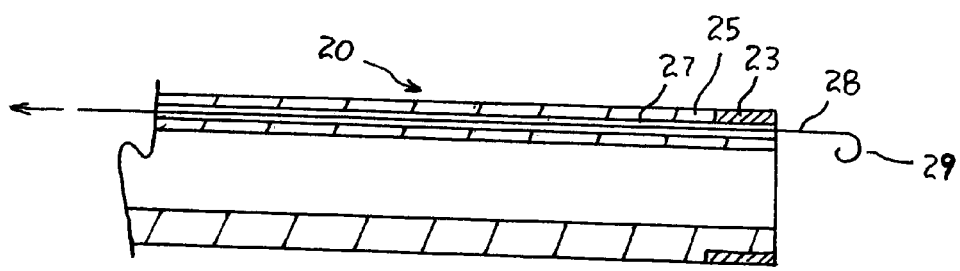
FIG. 7 is a cross section side view of the catheter shown in FIG. 6 with a resilient fiber core having a precurved distal segment being pulled into the channel in the wall of the catheter.
Figure 8:
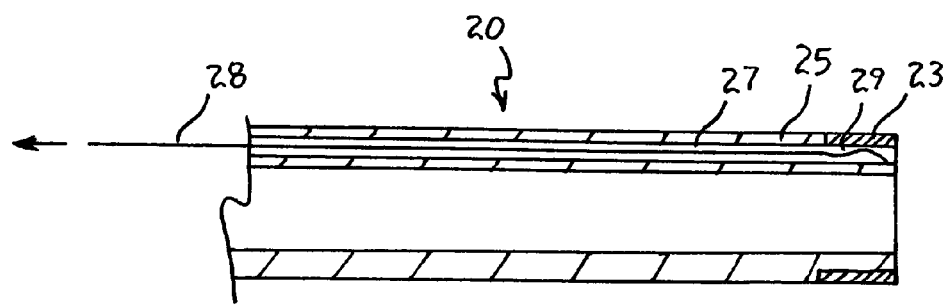
FIG. 8 is a cross section view of the catheter shown in FIG. 7 with the resilient fiber core positioned with its precurved distal segment contained within the stiffened segment of the catheter provided by the marker band.

The catheter 20 has a primary lumen 26 and a channel 27 formed in the wall of the primary lumen 26. A resilient fiber 28 having a precurved distal segment 29 is inserted into the channel 27 and pulled into the catheter 20 as shown in FIG. 7. The precurved segment 29 of the resilient fiber 28 is straightened when it is pulled into the catheter 20, as shown in FIG. 8. The now straightened segment 29 of the resilient fiber 28 is short enough that it can be contained within the section of the channel 27 that lies within the stiffened section of the catheter 20 formed by the marker band 23. Since the catheter 20 is stiff in this section as a result of the hard polymer used to create the marker band 23, the resilient filament 28 will be maintained in a straightened orientation while it resides within this section of the catheter 20. The catheter 20 can then be easily navigated into the body.

Figure 9:
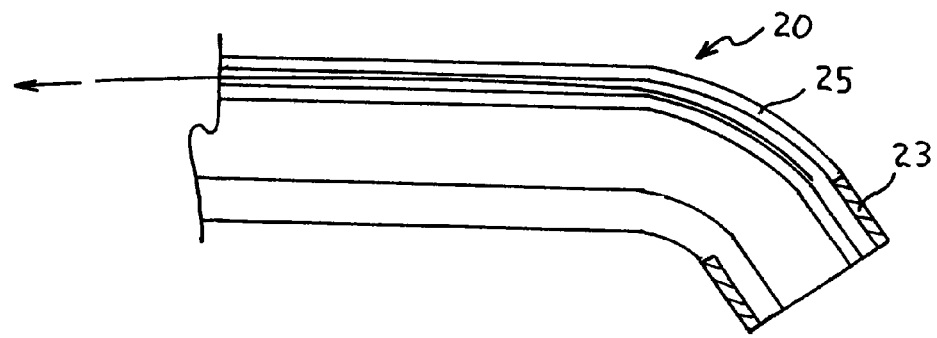
FIG. 9 is a cross section view of the catheter shown in FIG. 7 with the precurved distal segment of the resilient fiber core being pulled into the soft section of the catheter proximal the marker band.

Once the catheter 20 is navigated into position, the resilient fiber 28 can be pulled back so that the precurved portion 29 of the resilient fiber 28 is pulled into the soft section 25 of the catheter 20 just proximal the hard section 23. Once this occurs, the resilient fiber 28 will overcome the bending resistance of the soft section 25 and will impart a curve to the catheter 20 as shown in FIG. 9. Once the procedure is completed, the resilient fiber 28 is pulled out and the now straight catheter 20 is easily removed.

Figure 10:
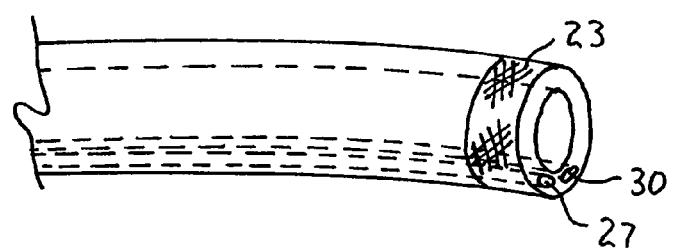
FIG. 10 is perspective view of a modified catheter according to a second embodiment of the present invention in which a second channel is provided in the wall of the catheter for receiving a second resilient fiber for fine tuning the catheter's position within the body.

A second channel 30, as shown in FIG. 10, can be provided in the catheter 20 adjacent to the first channel 27. A second resilient fiber (not shown) can then be slid into the second channel 30 after the curve is imparted to the catheter 20 by the first resilient fiber 28. The second resilient fiber can be used to temporarily straighten the catheter 20 to "fine tune" its position in the body.

The catheters 10 and 20 described above according to the first and second embodiments of the invention will be extremely useful in neurovascular applications where it is necessary to insert a straight catheter to the site and then introduce a curve after the catheter reaches the site.

While the invention has been specifically described in connection with specific embodiments thereof, it is to be understood that this is by way of illustration and not of limitation, and the scope of the appended claims should be construed as broadly as the prior art will permit.

What is claimed is:

1. A method for curving a catheter, comprising:
providing a resilient fiber with a preformed curve shape in a portion thereof;
providing a catheter having a first channel, a hard polymer ring that creates a stiffened section extending along a distal portion of the catheter, and a soft section proximal of the stiffened section which has a lower bending resistance than the stiffened section:
inserting the resilient fiber into the first channel of the catheter with the preformed portion of the resilient fiber contained substantially within a length of the stiffened section of the catheter created by the hard polymer ring with the preformed portion of the resilient fiber maintained in a straightened orientation within said stiffened section;
deploying the catheter to a desired location within a body; and
pulling the resilient fiber in a proximal direction within the first channel until at least part of the preformed portion of the resilient fiber slides out of the stiffened section created by the hard polymer ring and into the soft section and thereby imparts a curve shape to the catheter;
wherein the hard polymer ring is a cylindrical-shaped marker band provided at a distal end of the catheter.

2. A method for curving a catheter, comprising:
providing a resilient fiber with a preformed curve shape in a portion thereof;
providing a catheter having a first channel, a hard polymer ring that creates a stiffened section extending along a distal portion of the catheter, and a soft section proximal of the stiffened section which has a lower bending resistance than the stiffened section;
inserting the resilient fiber into the first channel of the catheter with the preformed portion of the resilient fiber contained substantially within a length of the stiffened section of the catheter created by the hard polymer ring with the preformed portion of the resilient fiber maintained in a straightened orientation within said stiffened section;
deploying the catheter to a desired location within a body; and
pulling the resilient fiber in a proximal direction within the first channel until at least part of the preformed portion of the resilient fiber slides out of the stiffened section created by the hard polymer ring and into the soft section and thereby imparts a curve shape to the catheter;
further comprising the steps of:
providing a second channel adjacent to the first channel; and
sliding a second resilient fiber into the second channel to temporarily straighten the catheter to adjust its position within the body.

3. A method for curving a catheter, comprising:
providing a resilient fiber with a preformed curve shape in a portion thereof;
providing a catheter having a first channel, a hard polymer ring that creates a stiffened section extending along a distal portion of the catheter, and a soft section proximal of the stiffened section which has a lower bending resistance than the stiffened section;
inserting the resilient fiber into the first channel of the catheter with the preformed portion of the resilient fiber contained substantially within a length of the stiffened section of the catheter created by the hard polymer ring with the preformed portion of the resilient fiber maintained in a straightened orientation within said stiffened section;
deploying the catheter to a desired location within a body; and
pulling the resilient fiber in a proximal direction within the first channel until at least part of the preformed portion of the resilient fiber slides out of the stiffened section created by the hard polymer ring and into the soft section and thereby imparts a curve shape to the catheter;
wherein the catheter further comprises a primary lumen adjacent to the first channel, and wherein said hard polymer ring has a cylindrical shape that extends along a length of the catheter and surrounds the primary lumen and the first channel.

4. A catheter that can be deployed with a curved shape, comprising:
a first channel, a hard polymer ring that creates a stiffened section extending along a distal portion of the catheter, and a soft section proximal of the stiffened section which has a lower bending resistance than the stiffened section;
a resilient fiber with a preformed curve shape in a portion thereof, said fiber being disposed within the first channel and slidable therein between a first position in which the preformed portion of the resilient fiber is contained substantially within a length of the stiffened section of the catheter created by the hard polymer ring and is maintained in a straightened orientation within said stiffened section, and a second position in which at least part of the preformed portion of the resilient fiber is pulled in a proximal direction out of the stiffened section created by the hard polymer ring and into the soft section and thereby imparts a curve shape to the catheter;
wherein the hard polymer ring is a cylindrical-shaped marker band provided near a distal end of the catheter.

5. A catheter that can be deployed with a curved shape, comprising:
a first channel, a hard polymer ring that creates a stiffened section extending along a distal portion of the catheter, and a soft section proximal of the stiffened section which has a lower bending resistance than the stiffened section;
a resilient fiber with a preformed curve shape in a portion thereof, said fiber being disposed within the first channel and slidable therein between a first position in which the preformed portion of the resilient fiber is contained substantially within a length of the stiffened section of the catheter created by the hard polymer ring and is maintained in a straightened orientation within said stiffened section, and a second position in which at least part of the preformed portion of the resilient fiber is pulled in a proximal direction out of the stiffened section created by the hard polymer ring and into the soft section and thereby imparts a curve shape to the catheter;
further comprising a primary lumen adjacent to the first channel, and wherein said hard polymer ring surrounds the primary lumen and the first channel.

6. A catheter that can be deployed with a curved shape, comprising:
a first channel, a hard polymer ring that creates a stiffened section extending along a distal portion of the catheter, and a soft section proximal of the stiffened section which has a lower bending resistance than the stiffened section;
a resilient fiber with a preformed curve shape in a portion thereof, said fiber being disposed within the first channel and slidable therein between a first position in which the preformed portion of the resilient fiber is contained substantially within a length of the stiffened section of the catheter created by the hard polymer ring and is maintained in a straightened orientation within said stiffened section, and a second position in which at least part of the preformed portion of the resilient fiber is pulled in a proximal direction out of the stiffened section created by the hard polymer ring and into the soft section and thereby imparts a curve shape to the catheter;

further comprising a second channel and a second resilient fiber which is slidable within the second channel to temporarily straighten the catheter to adjust its position within the body.

* * * * *